United States Patent
Schläpfer et al.

(10) Patent No.: US 7,008,432 B2
(45) Date of Patent: Mar. 7, 2006

(54) DEVICE FOR DISTRACTING OR COMPRESSING BONES ON BONE FRAGMENTS

(75) Inventors: Fridolin Schläpfer, Glarus (CH); Martin Hess, Hölstein (CH)

(73) Assignee: Synthes, West Chester, PA (US)

( * ) Notice: Subject to any disclaimer, the term of this patent is extended or adjusted under 35 U.S.C. 154(b) by 0 days.

(21) Appl. No.: 10/165,069

(22) Filed: Jun. 10, 2002

(65) Prior Publication Data

US 2003/0187453 A1    Oct. 2, 2003

Related U.S. Application Data

(63) Continuation of application No. PCT/CH99/00598, filed on Dec. 10, 1999.

(51) Int. Cl.
*A61B 17/66* (2006.01)

(52) U.S. Cl. .......................... 606/90; 606/105
(58) Field of Classification Search ............. 606/86, 606/90, 105, 206, 207, 210; 600/210, 213, 600/217, 227
See application file for complete search history.

(56) References Cited

U.S. PATENT DOCUMENTS

| | | | | |
|---|---|---|---|---|
| 1,170,334 A | * | 2/1916 | Riggs | ................ 81/303 |
| 2,002,021 A | * | 5/1935 | Rouse | ............... 606/105 |
| 3,750,652 A | | 8/1973 | Sherwin | ............... 128/17 |
| 3,840,003 A | * | 10/1974 | Komiya | ............... 600/564 |
| 4,898,161 A | | 2/1990 | Grundei | ............... 606/105 |
| 5,122,130 A | * | 6/1992 | Keller | ............... 606/61 |
| 5,755,661 A | * | 5/1998 | Schwartzman | ........... 600/216 |
| 6,017,342 A | * | 1/2000 | Rinner | ............... 606/57 |
| 6,712,825 B1 | * | 3/2004 | Aebi et al. | ............. 606/90 |

FOREIGN PATENT DOCUMENTS

DE          44 09 939 A1        3/1994

* cited by examiner

*Primary Examiner*—David O. Reip
(74) *Attorney, Agent, or Firm*—Jones Day

(57) ABSTRACT

The invention relates to a device for exerting axial forces on bone fragments or vertebral bodies. The inventive device comprises a first connecting element, a second longitudinal connecting element which is displaceable relative to the first connecting element and a longitudinal support with a longitudinal axis and a front end that can be linked with the first connecting element. A tubular sleeve is coaxial relative to the longitudinal axis in which the longitudinal support is displaceable parallel to the longitudinal axis and comprises a front end that is directed against the first connecting element. At least one first lever rotatably links the front end and the second connecting element and at least one second lever is rotatably disposed on the first connecting element and on the second connecting element so that a relative movement between the front end and the first connecting element results in a relative movement between the first and the second connecting elements along a line that substantially extends traversely to the longitudinal axis.

42 Claims, 4 Drawing Sheets

DEVICE FOR DISTRACTING OR COMPRESSING BONES ON BONE FRAGMENTS

CROSS-REFERENCE TO RELATED APPLICATION

This application is a continuation of the U.S. National Stage designation of International Patent Application PCT/CH99/00598, filed Dec. 10, 1999. The entire content of this application is expressly incorporated herein by reference thereto.

FIELD OF THE INVENTION

This invention relates to a system or device for applying axial forces on at least two bone fragments or vertebral bodies with which the device can be connected.

BACKGROUND OF THE INVENTION

For example, if a vertebra is diseased or damaged, it may have to be removed from the spine. In place of that vertebra a spacer implant is grafted in. Implants usually encompass mutually shiftable components as well as two special end plates serving to anchor the implant in the adjoining healthy vertebrae. In many other cases an internal fixation system is attached in a manner whereby it connects two vertebrae, with the fixation system bridging one or even several defective vertebrae. In the case of these predominantly plate-shaped implants the end-plate sections are fastened to the vertebrae by means of bone screws. The connecting elements between the end-plate sections are of a telescoping design, allowing the vertebrae next to the defective vertebral bodies to move parallel to the spinal axis in expansile or contractile fashion. Yet other spinal fixation systems consist of rod-shaped longitudinal supports that can be attached to pedicle screws via connecting elements. These connecting elements are so designed that they can slide along the longitudinal supports in an axial direction, again permitting expansile and contractile movement between the vertebrae. These provisions often require a distracting or compression of vertebrae or implant segments by means of appropriate instruments.

A device for distracting vertebrae has been described in U.S. Pat. No. 4,898,161 by GRUNDEI. This earlier distracting device features a pincer-like design of two levers axially extending into two jaws that can be equipped with pins. The jaws include special guide yokes and move in a parallel direction to each other when the pincers are opened or closed. By means of an adjustable bolt-and-nut joint between the two levers the pincer-like distracting device can be locked in position. A shortcoming of that earlier distracting device lies in its inability to produce any compressive displacement.

This invention is designed to remedy that problem. Adavantageously, this invention provides a device capable of distracting and compressing bone fragments, vertebral bodies or implant sections while at the same time permitting a very precise fine adjustment of the jaw spacing.

The invention achieves this by means of a device for applying axial forces on at least two bone fragments or vertebrae to which the device is connected.

SUMMARY OF THE INVENTION

The present invention relates to a device comprising the following:

A) a first connecting element, extending along a longitudinal axis and designed to connect to a bone fragment or vertebra;

B) a second connecting element, extending along a longitudinal axis and designed to connect to another bone fragment or vertebra, with the longitudinal axes defining a plane and the second connecting element being movable relative to the first connecting element in a way as to cause the latter's longitudinal axis to move within the said plane;

C) a longitudinal support, extending coaxially with the longitudinal axis of the first connecting element, with a back end as well as a front end that can be connected to the first connecting element, its longitudinal axis extending parallel to the said plane;

D) a tubular sleeve, extending coaxially with the longitudinal axis and provided with a coaxial end-to-end bore in which the longitudinal support can slide parallel to the said longitudinal axis, and equipped with a forward end piece that faces the first connecting element, as well as a rearward end piece;

E) at least one first lever, having a longitudinal axis that extends essentially parallel to the said plane and connects the forward end piece to the second connecting element, said lever being pivotably mounted on the end piece in such fashion that the longitudinal axis can be rotated essentially parallel to the said plane; and F) at least one second lever whose longitudinal axis extends essentially parallel to the said plane and which is so connected in pivotable fashion to the first connecting element and to the second connecting element that the longitudinal axis can be rotated essentially parallel to the said plane; whereby G) a relative movement between the forward end piece and the first connecting element parallel to the longitudinal axis results in a relative movement between the first and the second connecting element along a line or curve that extends parallel to the said plane and in an essentially transverse direction relative to the longitudinal axis.

The longitudinal axes of the two levers intersect at a crossover point and are rotatably connected to each other by means of a pivot joint provided at that point of intersection. The levers may also be attached in pairs in which case the respective first and second set of levers include each one pair of levers opposite the sleeve and the connecting element. On the other hand, the first and second set of levers may also include on the same side of the sleeve or, respectively, of the connecting elements two or several levers that can extend in a parallel direction.

The longitudinal support may be designed in simple fashion to permit its axial movement within the sleeve, for which purpose the longitudinal support and the sleeve can be manipulated via simple handles or levers mounted on these elements. In another embodiment, the longitudinal support and the sleeve can be moved parallel to the longitudinal axis and relative to each other by means of a lever mechanism. Mounted on the longitudinal support and on the sleeve, perpendicular to the longitudinal axis, are rigid levers which by means of a pincer-like device can be moved toward or away from each other. Swivel joints connect the rigid levers to the pincer levers which intersect at a common pivot joint, whereby a squeezing of the pincer levers moves the rigid levers against each other. Forcing the pincer levers apart is accomplished by means of a spring mounted between them.

In another embodiment of the device according to this invention, the longitudinal support is provided, in an area (B) opposite the forward end piece on the sleeve, with a male thread that matches a corresponding female thread on the forward end piece of the sleeve. The longitudinal support is pivot-mounted in the first connecting element so as to permit rotation around the longitudinal axis while in an axially fixed position relative to the longitudinal axis. In this fashion the relative movement, axial in the direction of the longitudinal axis, between the longitudinal support and the sleeve is generated by a rotation of the longitudinal support within the sleeve.

Alternatively, the longitudinal support may be provided, in an area (C) at its forward end that can be connected to the first connecting element, with a second male thread which allows the first connecting element to be connected to the forward end of the longitudinal support via a matching female thread.

The threads may run in the same direction but at a different pitch, or in opposite directions whereby one male thread is a right-hand thread while the other male thread is a left-hand thread. The corresponding female threads are suitably matched. Multiple-thread versions are also possible.

The levers may be attached to both connecting elements in rotatable fashion. If in addition a fulcrum of a lever is movable on a connecting element parallel to the longitudinal axis of the connecting element, a shift between the connecting elements relative to each other is possible, while the longitudinal axes of the connecting elements remain parallel and the connecting elements extend along a straight line perpendicular to their longitudinal axes.

The first lever or levers may also be rigidly attached to the corresponding connecting elements in which case the connecting elements move relative to each other along a flat curve.

The advantageous features made possible by this invention comprise a novel device that permits both distracting and compressing action with one and the same equipment even over substantial distracting or compression distances while ensuring a parallel movement of the bone fragments, vertebrae or implant sections. Moreover, the device permits the feed-through of a graft-specific tool or instrument and for instance of a screwdriver as well.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
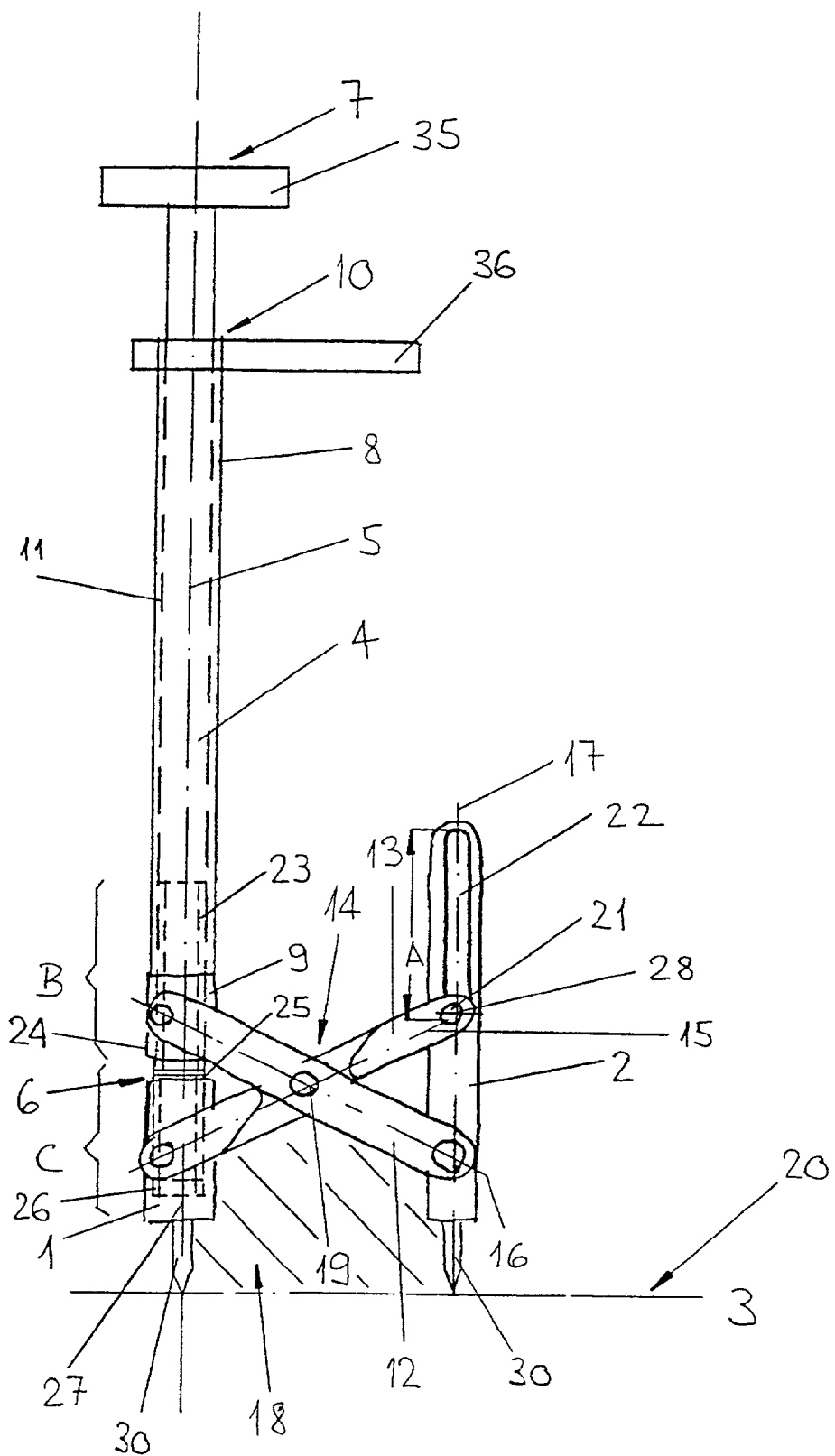
FIG. 1 illustrates one embodiment of the device according to the invention.

One embodiment of the device according to this invention is illustrated in FIG. 1 and encompasses a first connecting element 1, with a longitudinal axis 27, that can connect to a bone fragment or vertebra, and a second longitudinal connecting element 2, with a longitudinal axis 17, that can connect to another bone fragment or vertebra. The longitudinal axes 17, 27 of the connecting elements define a plane 18. On the side facing the bone or implant the connecting elements 1, 2 are equipped with points 30 which can be brought up against bone fragments, vertebrae or implant sections and which, when the device is actuated, move along a straight line 3 positioned in the plane 18 and extending perpendicular to the longitudinal axes 17, 27. In addition, the second connecting element 2 can be moved relative to the first connecting element 1 in a manner whereby the longitudinal axis 17 travels along the plane 18 parallel to the longitudinal axis 27. For manipulating the device, the system is further equipped with a longitudinal support 4 which extends coaxially with the longitudinal axis 27 of the first connecting element 1 and, having a longitudinal axis 5 concentric with the longitudinal axis 27, features a back end 7 as well as a front end 6 that can be connected to the first connecting element 1. In this embodiment, the longitudinal axis 5 extends along the plane 18. A tubular sleeve 8, extending coaxially with the longitudinal axis 5 and provided with a coaxial end-to-end bore 11, permits the movement of the sleeve 8 coaxially with the longitudinal axis 5 along the longitudinal support 4. The sleeve 8 includes a forward end piece 9 that faces the first connecting element 1, and a rearward end piece 10. The movement of the two connecting elements 1, 2 relative to each other is generated by way of a first lever 12 that connects the forward end piece 9 to the second connecting element 2 and whose longitudinal axis 15 extends essentially parallel to the plane 18, said lever 12 connecting in pivotable fashion to the forward end piece 9 and to the second connecting element 2 in such fashion that, relative to the forward end piece 9 and to the second connecting element 2, the lever 12 can be swiveled, causing the longitudinal axis 15 to move parallel to the plane 18, while a second lever 13, with a longitudinal axis 16 extending essentially parallel to the plane 18, is pivotally connected to the first connecting element 1 and to the second connecting element 2, whereby the longitudinal axis 15 can be rotated parallel to the plane 18. The longitudinal axes 15, 16 of the two levers 12, 13 intersect at a crossover point 19 and are mutually connected via a swivel joint 14 located at the intersecting point 19. The scissor-like configuration of the levers 12, 13 makes it possible for a relative movement between the forward end piece 9 and the first connecting element 1 parallel to the longitudinal axis 5 to effect a movement, parallel to the longitudinal axes 17 and 27, between the first and the second connecting elements parallel to the straight line 3 that extends parallel to the plane 18 and perpendicular to the longitudinal axis 5.

The second connecting element 2 contains a guide 22 whereby the rotation of the second lever 13 relative to the second connecting element 2 is made around the longitudinal axis 28 of a pin 21 that is movable within the guide 22. This guide 22 extends parallel to the longitudinal axis 17 and has a length of A, permitting the pin 21 to move in the guide 22 parallel to the longitudinal axis 17.

The longitudinal support 4 is provided, in an area B opposite the forward end piece 9, with a first male thread 23 and the forward end piece 9 is provided with a female thread 24 matching the male thread 23. The longitudinal support 4 is additionally provided, in an area C at its front end 5 that can be connected to the first connecting element 1, with a second male thread 25 and the first connecting element 1 is attached to the front end 5 of the longitudinal support 4 via a female thread 26 that matches the second male thread 25. The male threads 23 and 25 on the longitudinal support 4 feature a mutually opposite pitch, with the male thread 25 in area C being a right-hand thread and the male thread 23 in area B being a left-hand thread. In analogous fashion, the female threads 24, 26 in the forward end piece 9 and in the first connecting element 1 have a mutually opposite pitch. As a result, when the longitudinal support 4 is rotated around the longitudinal axis 5, the forward end piece 9 of the sleeve 8 and the first connecting element 1 will move toward or away from each other, depending on the direction of rotation of the longitudinal support 4. This relative movement of the forward end piece 9 and the first connecting element 1 results in the relative movement between the two connecting elements 1, 2. For a rotation between the longitudinal support 4 and the sleeve 8, the back end 7 of the longitudinal support 4 is provided with a first handle 35 and the back end 10 of the sleeve 8 on its part is provided with a second handle 36.

The longitudinal support 4 and the first connecting element 1 may be provided with bores extending coaxially with their longitudinal axes 5, 27, permitting the insertion of a screwdriver through these bores. Similarly, the second connecting element 2 may be provided with a bore coaxially with its longitudinal axis 17, again permitting the insertion of a screwdriver through that bore.

Figure 2:
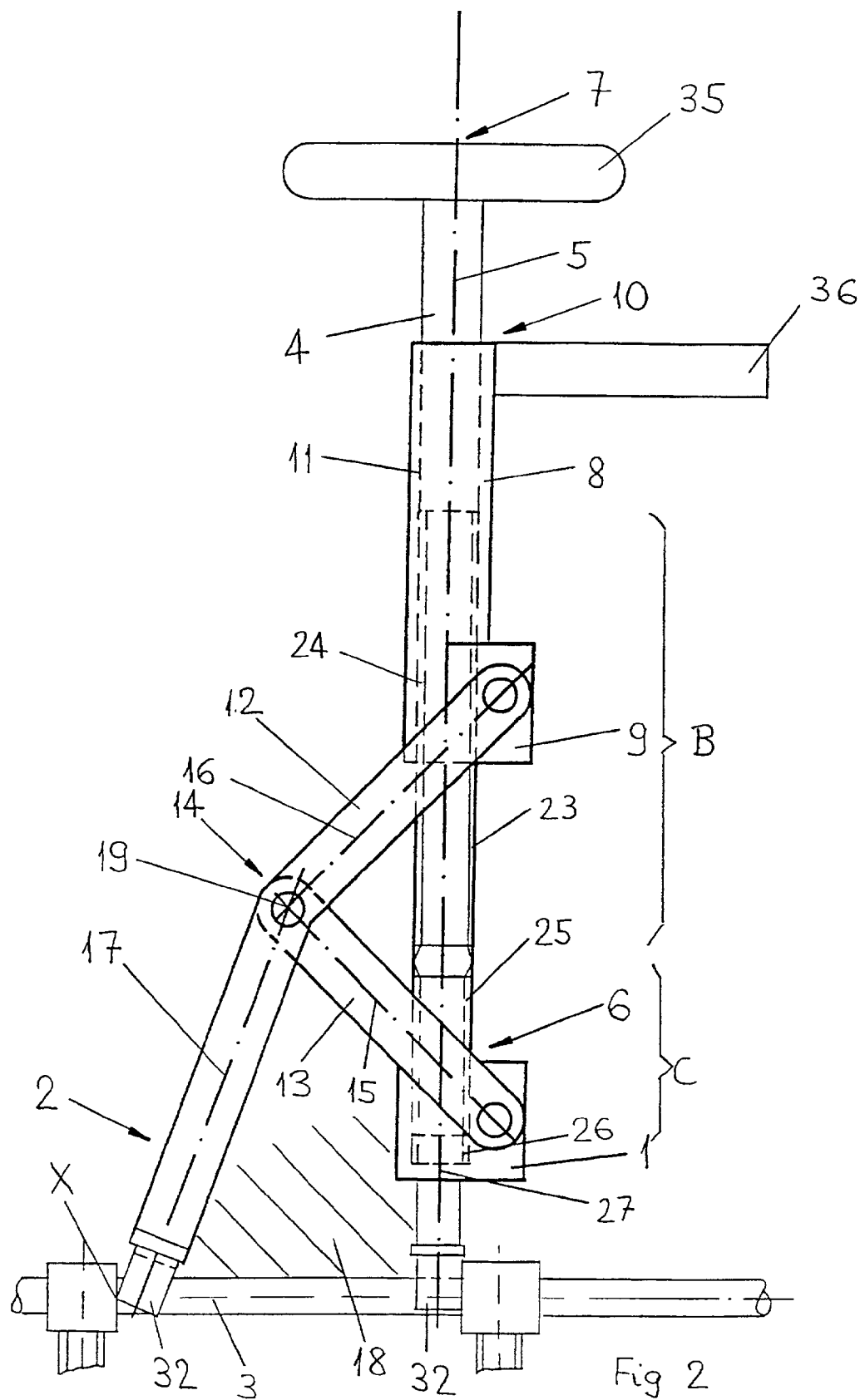
FIG. 2 shows another embodiment of the device according to the invention.

The embodiment of the device according to this invention illustrated in FIG. 2 differs from the design in FIG. 1 only in that the longitudinal axes 15, 16 of the two levers 12, 13 intersect at the far end, respectively relative to the forward end piece 9 and the first connecting element, of the levers 12, 13. Accordingly, the swivel joint 14 connecting the two levers 12, 13 is located at these ends.

The levers 12, 13 are essentially of the same length. The second connecting element 2 is rigidly attached to the first lever 12, with the longitudinal axis 16 of the lever 12 and the longitudinal axis 17 of the second connecting element 2 intersecting at an angle. When this design version of the device according to the invention is actuated, the connecting elements 1, 2 do not move with their longitudinal axes 17, 27 remaining parallel. Instead, the connecting elements 1, 2 move along a curve extending along the plane 18. It is possible, however, to define on the second connecting element 2 a point X which moves essentially along a straight line 3 parallel to the plane 18. The connecting elements 1, 2 are equipped with U-shaped plates 32 that can be brought in contact with implant or graft sections.

Figure 3:
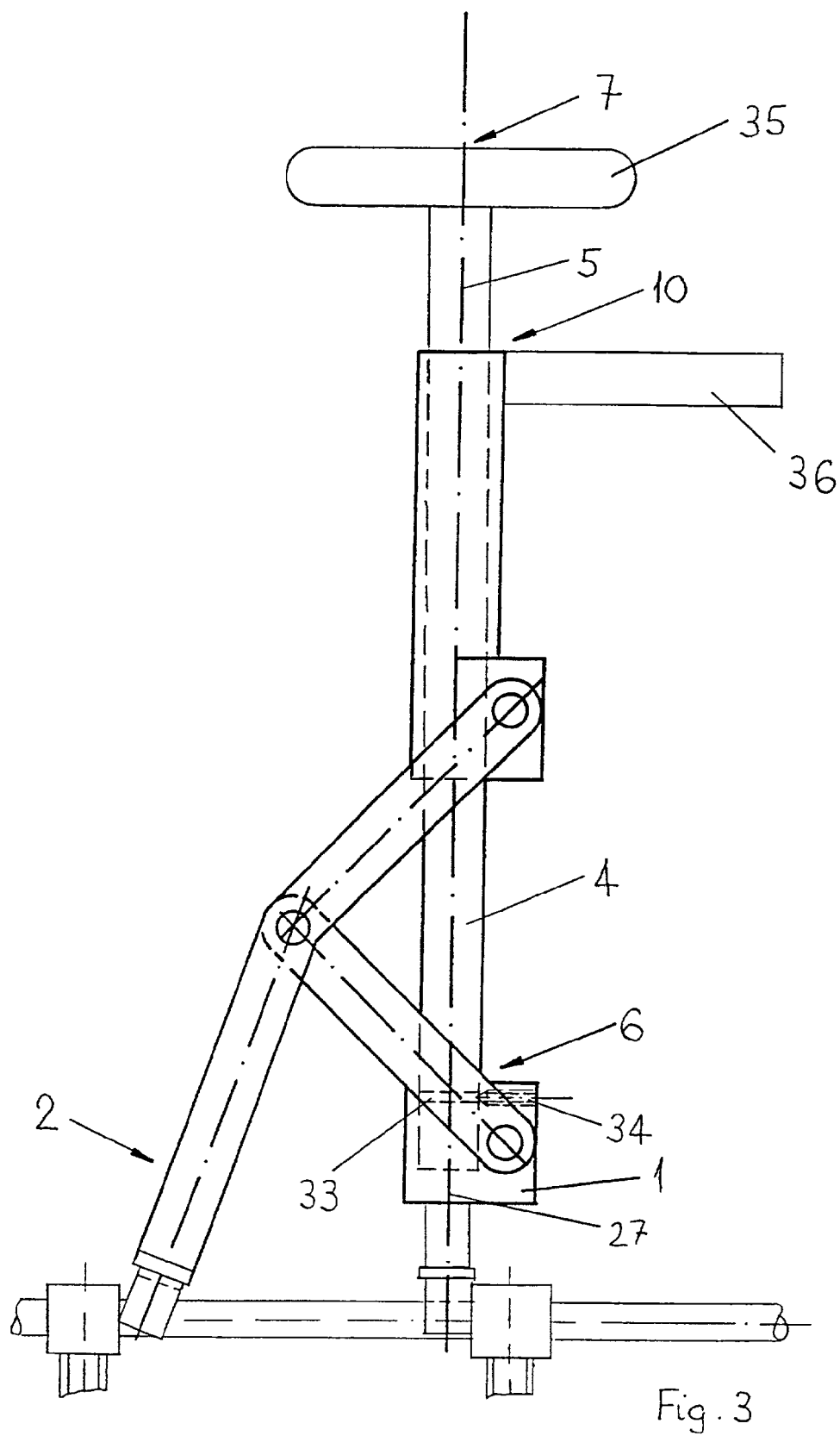
FIG. 3 depicts yet another embodiment of the device according to the invention.

FIG. 3 depicts another embodiment of the device according to this invention that differs from the embodiment of FIG. 2 only to the extent that the longitudinal support 4 can be moved in the sleeve 8 parallel to the longitudinal axis 5 and that its front end 6 is supported in the first connecting element 1 in an axially fixed position relative to the longitudinal axis 27 while permitting rotation around the longitudinal axis 27. In this fashion, the relative movement between the longitudinal support 4 and the sleeve 8 constitutes a purely axial shift attainable by pushing the handles 35 and 36 toward or, respectively, away from each other. The rotatable yet axially fixed attachment of the longitudinal support 4 in the first connecting element 1 is obtained by means of a set-screw 34 that is screwed into the first connecting element 1 and protrudes into a corresponding groove 33 in the longitudinal support 4.

The motion transfer mechanism between the longitudinal support 4 and the sleeve 8 can just as easily be employed in the embodiment of the device illustrated in FIG. 1

Figure 4:
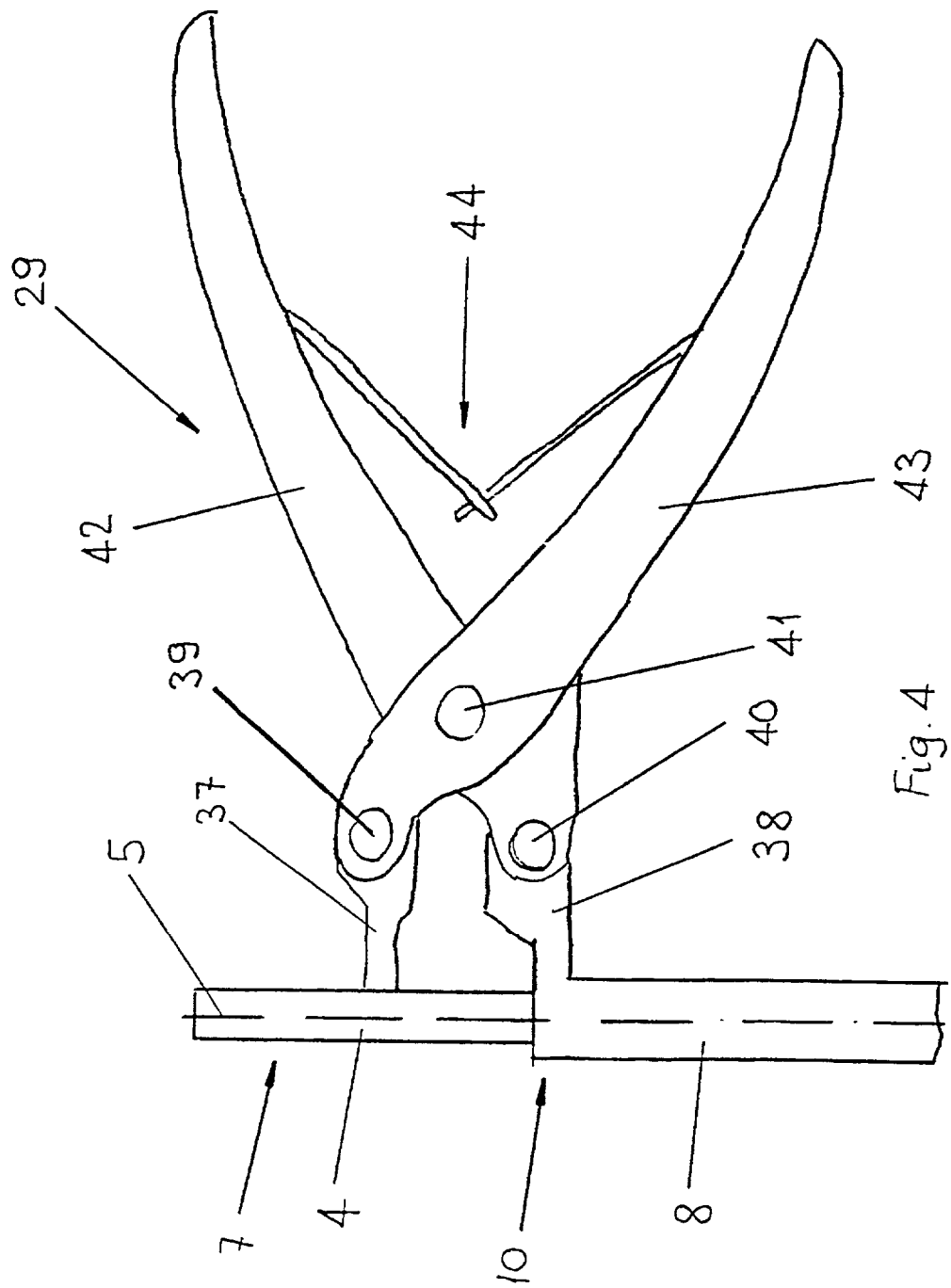
FIG. 4 shows a pincer-like actuating device for manipulating the individual embodiments of the device according to the invention.

FIG. 4 is a partial view of an embodiment of the device according to this invention for manipulating the individual embodiments of the device, for instance the embodiment of FIG. 3, in which the longitudinal support 4 and the sleeve 8 can be shifted, by means of a lever mechanism 29, both parallel to the longitudinal axis 5 and relative to each other. Attached to the ends 7 and 10 of the longitudinal support 4 and the sleeve 8, in a position perpendicular to the longitudinal axis 5, are fixed levers 37 and 38 which by means of a pincer mechanism can be moved toward or away from each other. The pincer levers 42 and 43 are attached to the fixed levers 37 and 38 via swivel joints 39 and 40 and intersect at a common swivel joint 41, whereby a squeezing of the pincer levers 42 and 43 causes the levers 37 and 38 to move toward each other. A spring 44 positioned between them serves to pull the pincer levers 42 and 43 apart.

One of ordinary skill in the art can envision numerous variations and modifications to the invention disclosed herein. All of these modifications are contemplated by the true spirit and scope of the following claims.

The invention claimed is:

1. A system for applying axial forces on at least two bone fragments or vertebrae to which the system can be connected, comprising
   A) a first connecting element, with a first longitudinal axis, that can be connected to a bone fragment or a vertebral body, and
   B) a second longitudinal connecting element, with a second longitudinal axis, that can be connected to another bone fragment or vertebra, with the first and second longitudinal axes defining a plane while the second connecting element is movable relative to the first connecting element in a manner whereby the second longitudinal axis travels within the plane;
   wherein the system
   C) also includes, coaxially with the first longitudinal axis, a longitudinal support with a third longitudinal axis, a back end and a front end that can be connected to the first connecting element, with the third longitudinal axis extending parallel to the plane;
   D) includes a tubular sleeve that extends coaxially with the third longitudinal axis and is provided with a coaxial end-to-end bore within which the longitudinal support, featuring a forward end piece that faces the first connecting element as well as a rearward end piece, is movable parallel to the third longitudinal axis;
   E) comprises a first lever that connects the forward end piece to the second connecting element, that has a fourth longitudinal axis that extends essentially parallel to the plane and which is attached to the end piece in rotatable fashion, whereby the fourth longitudinal axis can be swiveled in a direction essentially parallel to the plane; also
   F) includes at least one second lever having a fifth longitudinal axis extending essentially parallel to the plane and which is pivotably attached to the first connecting element and to the second connecting element in a manner whereby the fifth longitudinal axis can be swiveled essentially parallel to the plane, so that
   G) a relative movement between the forward end piece and the first connecting element parallel to the third longitudinal axis produces a relative movement between the first and the second connecting element along a line that extends parallel to the plane and essentially in a transverse direction relative to the third longitudinal axis.

2. The system as in claim 1, wherein the term parallel to the plane signifies in the plane.

3. The system as in claim 2, wherein the line is a straight line.

4. The system as in claim 3, wherein on the second connecting element a point is defined which during the relative movement between the forward end piece and the first connecting element travels essentially along the straight line that extends essentially parallel to the plane.

5. The system as in claim 4, wherein the straight line extends in a direction perpendicular to the third longitudinal axis.

6. The system as in claim 5, wherein the fourth and fifth longitudinal axes intersect at a crossover point.

7. The system as in claim 6, wherein the levers are connected to each other by means of a swivel joint positioned at the crossover point.

8. The system as in claim 7, wherein the levers are of essentially the same length.

9. The system as in claim 8, wherein the second connecting element can be shifted relative to the first connecting element in an essentially parallel direction.

10. The system as in claim 9, wherein the second connecting element can be shifted relative to the first connecting element in a direction essentially parallel to the third longitudinal axis.

11. The system as in claim 10, wherein the first lever is pivotably attached to the second connecting element in a manner whereby the fourth longitudinal axis can be rotated in a direction essentially parallel to the plane.

12. The system as in claim 11, wherein the second connecting element includes a guide and that the rotation of the second lever relative to the second connecting element takes place around a sixth longitudinal axis of a pin that is movably positioned in the guide.

13. The system as in claim 12, wherein, parallel to the second longitudinal axis, the guide is of a length that allows the pin to move in the guide parallel to the second longitudinal axis.

14. The system as in claim 8, wherein the second connecting element and the first lever are rigidly connected to each other.

15. The system as in claim 14, wherein the levers form an isosceles triangle.

16. The system as in claim 15, wherein
A) the longitudinal support is provided with a male thread opposite the forward end piece;
B) the forward end piece is provided with a female thread matching the male thread;
C) the longitudinal support is pivotably attached to the first connecting element in a way as to permit its rotation around the third longitudinal axis; and
D) the longitudinal support is attached to the first connecting element in a position that is axially fixed relative to the third longitudinal axis.

17. The system as in claim 16, wherein the longitudinal support is attached to the first connecting element in an at least axially fixed position relative to the third longitudinal axis.

18. The system as in claim 17, wherein by means of a lever mechanism the longitudinal support and the sleeve can be shifted parallel to the third longitudinal axis and relative to each other.

19. The system as in claim 18, wherein the lever mechanism is configured in pincer-like fashion with a spring serving to elastically spread the lever mechanism apart.

20. The system as in claim 19, wherein the longitudinal support and the first connecting element are provided with bores coaxially with the first and third longitudinal axes, permitting the insertion of a screwdriver through these bores.

21. The system as in claim 20, wherein the second connecting element is provided with a bore coaxially with the second longitudinal axis, permitting the insertion of a screwdriver through said bore.

22. The system as in claim 21, wherein the connecting elements are equipped with points that can be connected to bone fragments, vertebrae or implant and graft sections.

23. The system as in claim 21, wherein the connecting elements are equipped with blades that can be brought in contact with bone fragments, vertebrae or implant and graft sections.

24. The system as in claim 21, wherein the connecting elements are equipped with U-shaped plates that can be brought in contact with implants or grafts.

25. The system as in claim 21, wherein
A) the junctions between the connecting elements and the implants such as bone screws which are solidly connected to the vertebrae or bone fragments, are designed in a form similar to ball-and-socket joints; and
B) the ball-and-socket-like junctions can be reversibly locked in an angularly fixed position.

26. The system as in claim 15, wherein
A) the longitudinal support is provided opposite the forward end piece with a first male thread;
B) the forward end piece is provided with a female thread that matches the male thread;
C) the longitudinal support is provided with a second male thread at its front end that can be connected to the first connecting element; and
D) the first connecting element can be connected to the front end of the longitudinal support by means of a female thread that matches the second male thread.

27. The system as in claim 26, wherein the male threads are equidirectional but differ in their pitch.

28. The system as in claim 26, wherein the male threads are mutually reversed.

29. The system as in claim 28, wherein at least one male thread is a right-hand thread.

30. The system as in claim 29, wherein at least one male thread is a left-hand thread.

31. The system as in claim 30, wherein the male thread is multi-pitched.

32. A system for distracting or compressing bone fragments comprising:
(A) a first connecting element configured to be operably connected to a first bone fragment;
(B) a second connecting element configured to be operably connected to a second bone fragment;
(C) a longitudinal support having a longitudinal axis and connected to a first handle;
wherein the longitudinal support is associated with the first connecting element;
wherein the second connecting element is pivotally associated with the longitudinal support; and
wherein the movement of the first handle axially along the longitudinal axis translates the second connecting element in a direction substantially transverse to the longitudinal axis.

33. The system of claim 32, further comprising a tubular sleeve encompassing at least a portion of the longitudinal support, the tubular sleeve connected to a second handle.

34. The system of claim 33, wherein the longitudinal support is rotatable within the tubular sleeve.

35. The system of claim 32, wherein the first and second connecting elements include bone screws.

36. The system of claim 32, wherein the first and second connecting elements include U-shaped structures.

37. The system of claim 32, further comprising a second handle connected to the longitudinal support.

38. The system of claim 32, wherein the first and second bone fragments are adjacent vertebrae.

39. The system of claim 32, wherein the first connecting element has a longitudinal axis, and wherein the longitudinal axes of the longitudinal support and the first connecting element are coaxial.

40. The system of claim 32, wherein the second connecting element has a longitudinal axis substantially parallel to the longitudinal axis of the longitudinal support.

41. The system of claim 32, wherein the first and second connecting elements are connected by a lever, and wherein the lever is pivotally associated with both the first and second connecting elements.

42. The system of claim 32, wherein the first connecting element is configured to be rigidly fixed to the longitudinal support.

* * * * *

UNITED STATES PATENT AND TRADEMARK OFFICE
CERTIFICATE OF CORRECTION

PATENT NO. : 7,008,432 B2
APPLICATION NO. : 10/165069
DATED : March 7, 2006
INVENTOR(S) : Schlapfer et al.

It is certified that error appears in the above-identified patent and that said Letters Patent is hereby corrected as shown below:

On Title page item 54 and col. 1, lines 1-3, Delete DEVICE FOR DISTRACTING OR COMPRESSING BONES ON BONE FRAGMENTS. Please insert Device for Distracting or Compressing Bones or Bone Fragments Signed and Sealed this Ninth Day of January, 2007

JON W. DUDAS
*Director of the United States Patent and Trademark Office*